United States Patent [19]
Helldin

[11] Patent Number: 5,593,386
[45] Date of Patent: Jan. 14, 1997

[54] NON-REUSABLE SYRINGE ADAPTED ROD-AND-PISTON UNIT AND METHOD FOR ASSEMBLING SUCH SYRINGE

[75] Inventor: Göran Helldin, Götene, Sweden

[73] Assignee: Dille Safe AB, As, Sweden

[21] Appl. No.: 360,813

[22] PCT Filed: Jul. 1, 1993

[86] PCT No.: PCT/SE93/00607

§ 371 Date: Dec. 29, 1994

§ 102(e) Date: Dec. 29, 1994

[87] PCT Pub. No.: WO94/01151

PCT Pub. Date: Jan. 20, 1994

[30] Foreign Application Priority Data

Jul. 2, 1992 [SE] Sweden ................................ 9202052

[51] Int. Cl.⁶ ........................................................... A61M 5/315
[52] U.S. Cl. ............................ 604/110; 604/218; 604/228
[58] Field of Search ........................................ 604/110, 187, 604/195, 196, 218, 228

[56] References Cited

U.S. PATENT DOCUMENTS

| | | | |
|---|---|---|---|
| 5,032,114 | 7/1991 | Olovson | 604/110 |
| 5,059,179 | 10/1991 | Quatrochi et al. | 604/110 |
| 5,141,495 | 8/1992 | Olovson | 604/218 |

FOREIGN PATENT DOCUMENTS 157085  10/1987  Norway.
WO92/18180  10/1992  WIPO.

*Primary Examiner*—Corrine M. McDermott
*Assistant Examiner*—Cris L. Rodriguez
*Attorney, Agent, or Firm*—Burns, Doane, Swecker & Mathis, L.L.P.

[57] ABSTRACT

The invention relates to a rod-and/or piston unit that can be enclosed in a container forming part of a non-reusable syringe where the rod and the piston have means for connecting the piston to the rod and disconnecting the piston therefrom. The piston and the rod are manufactured as one piece in a die or similar. The invention also relates to a method for assembling a syringe.

17 Claims, 1 Drawing Sheet

NON-REUSABLE SYRINGE ADAPTED ROD-AND-PISTON UNIT AND METHOD FOR ASSEMBLING SUCH SYRINGE

TECHNICAL FIELD

The present invention relates primarily to a rod-unit and a piston-unit which are adapted to coact detachably with one another when enclosed in a container so as to form a syringe that can be used only once.

To this end, it is necessary to provide the rod-unit and the piston-unit with means which will enable the units to be mutually connected and disconnected within the container by twisting the rod-unit and the piston-unit relative to one another.

The invention includes two separate methods of assembling a syringe intended for one-time use only, hereinafter referred to as a disposable syringe, which when assembled includes a rod-unit which is arranged for reciprocating movement in relation to a container and whose one end has the form of or coacts with a needle, a piston-unit which coacts with the rod-unit, and means which enable the piston-unit and rod-unit to be mutually connected and disconnected, said rod-unit and piston-unit being formed in accordance with the present invention.

BACKGROUND ART

Several different types of disposable injection syringes are known to the art. A disposable liquid-injection syringe is described in relative detail in International Patent Publication WO89/04677, in which the means used to connect and disconnect the piston and rod of the syringe have the form of screw-like means. The International Patent Publication includes exemplifying embodiments of rod and piston connecting means, where the embodiments illustrated in FIGS. 6 and 9 can be said to represent the closest prior art.

Other types of disposable injection syringes are also known to the art, for instance the syringe described and illustrated in Swedish prior Patent Publication SE-B-7902138-2, Publication No. 438,598.

The injection syringe described and illustrated in European Patent Application EP-A-2,229,017 also forms part of the prior art.

The rod configuration illustrated and defined in FIG. 7 of prior Patent Publication U.S. Pat. No. 5,004,460 also belongs to the prior art.

In addition to what is known from the aforecited publications, mention can be made to the different piston-unit and rod-unit connecting means illustrated and defined in prior publications U.S. Pat. No. 4,906,231 and FR-A-2,381,527 and NO-A-163,263.

The inventive syringe assembly is a development of the disposable syringe and the structural components illustrated and described in International Patent Application PCT/SE92/00258 filed on 21st Apr., 1992, and the reader is referred to this document for a closer understanding of the construction and forms of the rod-unit and piston-unit used in the present case and illustrated in the present Application.

DISCLOSURE OF THE PRESENT INVENTION

Technical Problems

When considering the earlier standpoint of techniques relating to liquid-injection syringes that are intended for one-time use only, referred to here as disposable or non-reusable syringes, it will be seen that a technical problem resides in creating conditions and providing rod-units and piston-units for such syringes in a form which will enable said units to be produced readily in large quantities, particularly by means of plastic moulding techniques or similar techniques, while maintaining a degree of accuracy and mutual conformity between said units which will satisfy the requirement of simple assembly and effective function.

It will also be seen that a technical problem is one of realizing the advantages that are afforded when the rod-unit and the piston-unit are formed as a one-piece structure.

When considering the earlier teachings of International Patent Publication WO89/004677 in particular, it will be seen that another technical problem is one of providing a rod-unit which is provided with a piston-unit connecting and disconnecting means, and a piston-unit which is provided with a rod-unit connecting and disconnecting means and which can both be readily produced in the form of an integrated one-piece structure, where an integrated unit structure is produced by injection moulding in a plastic moulding machine having a two-part matrix, such as by thermoplastic treatment or by thermoplastic moulding.

In this connection, a technical problem resides in realizing along which element lines along the rod-unit and the piston-unit and along said connecting and disconnecting means the matrix parts shall coact in order to facilitate and enable simultaneous moulding of the rod-unit and the piston-unit and their associated connecting and disconnecting means in a rational manner.

It will also be seen that a technical problem resides in realizing the technical assembly advantages that are afforded by shaping the rod-unit and the piston-unit in a two-part matrix in one and the same moulding sequence and to firmly join said units together through the medium of a thin, narrow joining element.

Another technical problem is one of realizing the significance of causing an extension of a centre line on the rod-unit to coincide with, or essentially coincide with, a centre line on the piston-unit.

It will also be seen that a technical problem resides in the ability of realizing the significance of orientating the rod-unit and the piston-unit in relation to one another so that the aforesaid joining element will be formed by opposing outer corner parts of the units, particularly peripherally orientated outer corner parts.

A related technical problem is then one of realizing that these corner parts should be arranged so as to slightly overlap within said element, and therewith to provide in the matrix a gap which will the material flow or yield necessary in order to form said joining element.

Another technical problem is one of realizing the importance of adapting each joining element so as to enable the element to be broken and/or melted-off when wishing to separate the units along said element.

It will also be seen that technical problem when using a prefabricated and integrated rod-and-piston unit is one of realizing those advantages that are afforded by a novel method of assembling a syringe, particularly a disposable syringe, with which the desired and necessary separation of the rod-unit from the piston-unit can be effected within the syringe container.

It will also be seen that another technical problem is one of realizing the advantages that are afforded by the use of a prefabricated and integrated rod-and-piston unit in the assembly of a syringe wherewith the desired unnecessary separation of the rod-unit from the piston-unit can be effected outside the syringe container.

Solution

The present invention relates primarily to a novel rod-unit and/or piston-unit which can be enclosed in a container that forms part of a disposable syringe, wherein the rod-unit and the piston-unit are provided on their mutually opposing ends with unit connecting and unit disconnecting means.

In the case of a disposable syringe of the kind defined in the introduction and comprising a rod-unit and piston-unit provided with said connecting and disconnecting means, it is proposed that the rod-unit and the piston-unit are produced simultaneously in the form of a single one-piece unit in a two-part mould or like tool, and that said rod and piston units are mutually joined by a readily destructed unit joining element.

According to further developments of the invention, an extension of a centre line on the rod-unit shall coincide with, or essentially coincide with, a centre line on the piston-unit.

The narrow element joining said rod-unit to the piston-unit will preferably consist of mutually opposing outer corner parts of the units, and more preferably peripherally orientated outer corner parts.

The corner parts will preferably overlap slightly in unit joining element. This is achieved by forming in the mould tool a narrow gap which can take-up the material flow or yield required to form the joining element between the units, said element being such as to enable it to be readily broken and/or melted-off when wishing to separate the units.

The invention also relates to a first method of assembling a disposable syringe which when assembled includes a rod which is intended to move reciprocatingly in relation to a container and one end of which is comprised of or can coact with a needle, a piston which is intended to coact with the rod-unit, and means for connecting and disconnecting the piston-unit to and from the rod-unit respectively.

In this first method, a prefabricated and integrated rod-and-piston unit is positioned so that an extension of a centre line on the integrated rod-unit and the piston-unit will coincide with, or essentially coincide with, an extension of a centre line on the container, and the integrated rod-and-piston unit is inserted into the container and the rod-unit then separated from the piston-unit, whereafter the unit connecting and disconnecting means are brought to a unit connecting position by twisting the rod-unit relative to the piston-unit.

The present invention also relates to a second method of assembling a syringe which when assembled includes a rod that is intended to move reciprocatingly in relation to a container and one end of which is comprised of or can coact with a needle, a piston which is intended to coact with the rod-unit, and means for connecting and disconnecting the piston unit to and from the rod-unit respectively.

In this regard, it is proposed that a prefabricated and integrated rod-and-piston unit is orientated for mutual separation of said units one from the other, that the separated units are positioned so that an extension of a centre line on the rod-unit and/or on the piston-unit coincides with, or essentially coincides with an extension of a container centre line, wherein the rod-unit and the piston-unit are inserted into the container and the means for connecting and disconnecting the piston to and from the rod are brought to a connecting position by twisting the two units relative to one another, either within the container or outside said container.

In the case of both of said methods, the units can be separated either with the aid of a separate device or by applying pressure in the direction of the aforesaid centre line.

For instance, the aforesaid units can be mutually separated with the aid of an ultrasonic device which operates at a frequency of 35 kHz.

It is also proposed that the means for connecting and disconnecting the piston to and from the rod can be brought to a connecting position by first moving the rod-unit towards the piston-unit and then twisting the rod-unit relative to the piston-unit.

Thus, the invention relates to a disposable syringe produced in accordance with one of the aforesaid methods while using a prefabricated integrated rod-and-piston unit.

Advantages

Those advantages primarily afforded by the present invention reside in the ability to produce effectively and rationally a prefabricated and integrated rod-and-piston unit and of utilizing this integrated rod-and-piston unit in different ways to assemble a disposable syringe which, when assembled, includes a rod which can be moved reciprocatingly in relation to a container and whose one end is comprised of or can coact with a needle, a piston which is intended to coact with the rod-unit, and means for connecting and disconnecting the piston-unit to and from the rod-unit respectively.

The primary characteristic features of a combined rod-and-piston unit in accordance with the present invention are set forth in the characterizing clause of the following Claim 1.

The primary characteristic features of a first method of assembling a syringe while using such an integrated rod-and-piston unit are set forth in the characterizing clause of the following Claim 6, while the characteristic features of a second method of assembling a syringe with the aid of an integrated rod-and-piston unit in accordance with the present invention are set forth in the characterizing clause of the following Claim 11.

A disposable syringe produced in accordance with the invention has the characteristic features set forth in Claim 16.

BRIEF DESCRIPTION OF THE DRAWINGS

An exemplifying embodiment of a rod-and-piston unit at present preferred and two methods of assembling a disposable syringe while using said unit will now be described in more detail with reference to the accompanying drawings, in which.

DESCRIPTION OF PROPOSED EMBODIMENTS

Since the present invention is a further development of a syringe that comprises a rod-unit and a piston-unit which mutually coact through the medium of means when twisted in a first direction and which are described and illustrated in the aforesaid National Patent Application PCT/SE92/00258, this patent application shall be taken to form part of the description of the present invention and to illustrate the function of a disposable syringe having means 6 which are orientated for mutual coaction between the rod and the piston.

Figure 1:
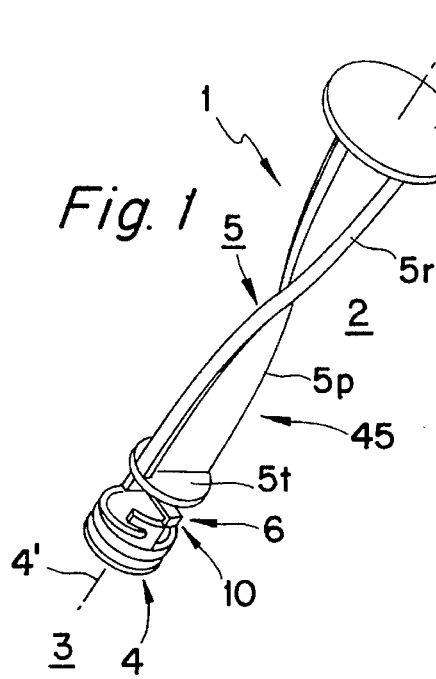
FIG. 1 is a perspective view of an integrated rod-and-piston unit intended for a syringe container, not shown.

FIG. 1 illustrates in perspective a rod-like device or a rod-unit 5 which is intended to be housed in a container 2 (not shown in FIG. 1) and the lower part of which, i.e. the part facing towards a needle 3 (not shown) is intended to coact with means formed in a piston 4.

The present invention thus provides, as FIG. 1 is intended to show, a novel form and a novel construction of an integrated rod-and-piston unit forming part of a liquid-injection syringe 1 which includes a container 2, a needle 3, a piston 4, the rod 5 and said means 6 which function to connect and disconnect the rod to and from the piston in response to relative movement therebetween.

Figure 2:
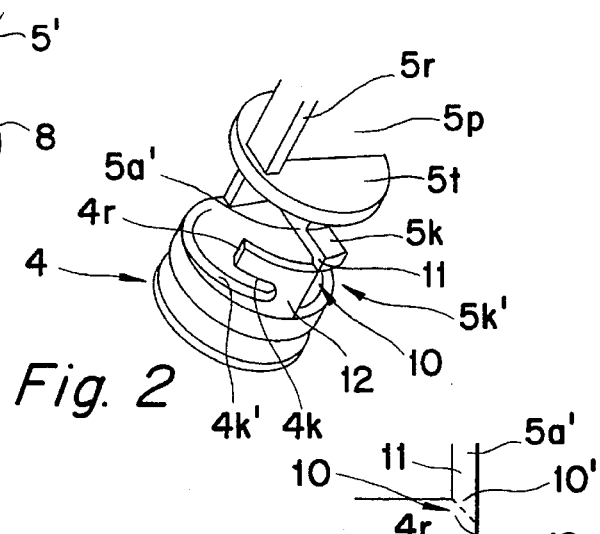
FIG. 2 is a larger scale perspective view of the connection between the integrated rod-and-piston unit significant to the invention, after producing the unit in a two-part mould.

According to the invention, the rod-unit 5 and the piston-unit 4 are produced as a one-piece, integrated structure or unit in a two-part mould, in which the two units are mutually joined by means of a unit joining element 10, as described in more detail below with reference to FIGS. 2 and 3.

According to the present invention, the two units are orientated so that an extension of a centre line 5' on the rod-unit 5 will coincide, or essentially coincide, with a centre line 4' on the piston-unit 4.

As shown in the drawing, the element 10 joining the rod-unit to the piston-unit is comprised of mutually joined and mutually facing outer corner parts, where the corner 11 of the part 5a' is joined to the corner 12 of the part 4r.

Figure 3:
FIG. 3 is an enlarged further view of the element that joins the rod-unit to the piston-unit.

As shown more clearly in FIG. 3, the corner parts 11, 12 are intended to overlap slightly within the element 10, which is effected by providing a peripherally orientated gap in the matrix to enable adapted flow of material between the units during the unit moulding process.

This unit joining element is adapted so as to be readily broken and/or melted-off when wishing to separate the units, for instance along a joining element 10'.

With regard to the size of the element 10 and the configuration of the gap, the element should be narrow enough to enable separation to be readily effected and the gap should be large enough to enable the hot plastic material to pass through the gap and fill the whole of the mould satisfactorily during the moulding operation.

The size of the gap will depend on the viscosity of the material, the temperature used, the pressure selected and other parameters. The requisite dimensions will be well known to the person skilled in this art.

The use of an integrated rod-and-piston unit of the aforedescribed kind enables a disposable syringe to be assembled in either one of two different ways, said syringe when assembled comprising a rod which can be moved reciprocatingly in relation to a syringe container and one end of which is comprised of or can coact with a needle, a piston that coacts with the rod-unit, and means for connecting and disconnecting the piston unit to and from the rod unit respectively.

Figure 4A:
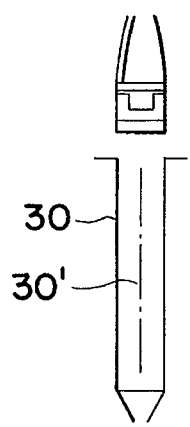
FIG. 4 illustrates a sequence of steps A–C in the manufacture of a disposable syringe, in which the rod-unit is separated from the piston-unit within actual the container.
Figure 4B:
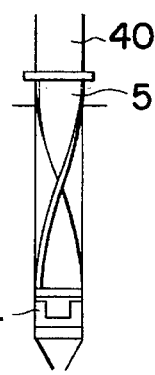
Figure 4C:
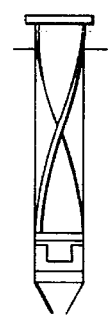

FIGS. 4A to 4C illustrate a method of utilizing an integrated rod-and-piston unit 45 according to FIG. 1, where FIG. 4A illustrates that an extension of a centre line 45' on the rod-and-piston unit is caused to coincide with, or essentially coincide with an extension of a centre line 30' on the container 30, so as to enable the integrated rod-and-piston unit 45 to be inserted into the container 30, as illustrated in FIG. 4B.

When the integrated unit has been inserted into the container, the rod-unit 5 can be separated from the piston-unit 4 along the element 10' and the unit connecting and disconnecting means brought to a unit connecting position by twisting the rod-unit 5 in a first direction relative to the piston-unit 4.

Figure 5A:
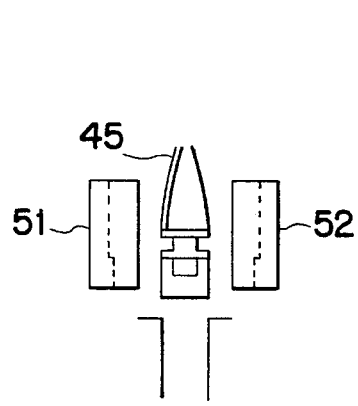
FIG. 5 illustrates a sequence of steps A–C in the manufacture of a disposable syringe in which the rod-unit is separated from the piston-unit outside the container.
Figure 5B:
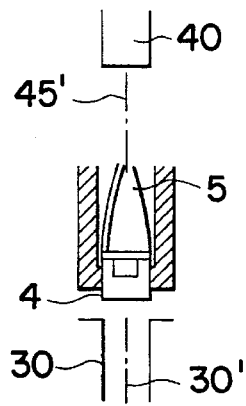
Figure 5C:
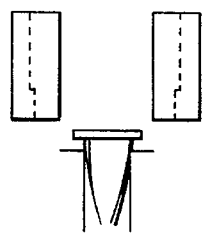

FIG. 5 illustrates another method which utilizes an integrated rod-and-piston unit 45 in which, as shown in FIG. 5A, the unit 45 is positioned so that the rod-unit and the piston-unit can be separated from one another prior to being inserted into the container.

The units 4, 5 separated along the element 10' are positioned so that an extension of a centre line 45' on the rod-unit and/or the piston-unit will coincide with, or essentially coincide with an extension of a centre line 30' on the container 30.

In this case, the piston-unit and the rod-unit are inserted into the container 30 and the means for connecting and disconnecting the piston with the rod are brought to an active connecting position either within the container or outside the same.

The two units are separated from each other by means of a separate device 40 in both of the aforesaid methods.

The two units are best separated by applying a small pressure in the direction of the centre line 45', i.e. by pressing the rod-unit 5 towards the piston-unit 4, or vice versa.

Separation along the joining element 10' can either be effected by breaking said element 10 or by melting-off said element. In this latter case, there may conveniently be used an ultrasonic unit, preferably an ultrasonic unit which operates at a frequency in the order of 35 kHz.

It is shown that the means for connecting the piston-unit to the rod-unit are brought to a connecting position by first moving the rod-unit 5 slightly towards the piston-unit 4 and then twisting the rod-unit in relation to the piston-unit through one-half turn, so as to cause the connecting means on the rod-unit to coact firmly with the connecting means on the piston-unit and therewith connect said units together.

As illustrated in FIGS. 4B and 5B, the separating device 40 is preferably constructed to melt the unit joining element 10' in a first working operation, and to move the rod-unit and the piston-unit closer together in a second working operation, and to twist the rod-unit relative to the piston-unit (or vice versa) in a third working operation, so as to achieve effective coaction between said means.

The first working operation is inactive during the second and the third working operations.

The second and the third working operations can be combined in a single working step.

The FIG. 5A embodiment includes clamping jaws 51 and 52 which are movable towards and away from each other and which subsequent to inserting an integrated unit 45 therebetween are moved towards one another so as to clamp firmly the piston-unit 4 but merely to guide the rod-unit 5.

The first working operation is carried out in the operational state shown in FIG. 5B.

The invention proposes the use of an ultrasonic melting device.

Such devices are known and utilize a generator-oscillator which generates a specific frequency, for instance a frequency of 20–40 kHz.

This oscillation is converted to mechanical motion. The amplitude is normally very small, in the order of hundredths of a millimeter. The plastic element 45 is placed in a jig which has three functions, namely the function of an anvil against axially acting forces, the function of guiding and clamping the lower part of the plastic element (in this case, the piston 4) radially, while solely guiding the upper part of the plastic element 45 so that said part is fixed against radial movement but free to move axially during the melting process.

The melting process is carried out when the oscillating device 40 is pressed against the upper part 5 of the plastic element. This upper part will then oscillate axially at the same frequency as the oscillating device. Because the lower part 4 of the plastic element is clamped firmly between said jaws (or at least dampened), there is a part 10 between the upper and lower element parts 4 and 5 in which frictional heat is generated.

Energy is developed relatively quickly and the plastic element will melt sufficiently to separate the units within the space of 0.1–0.2 seconds.

When wishing solely to separate the two parts 4, 5, one of said parts, the part 4, may be unsupported (not held in the jig). The intrinsic mass of this part will provide sufficient damping to obtain sufficient energy development in the narrow element 10 joining said parts. The plastic will melt solely within the region of this element and enable the parts 4, 5 to be easily separated.

The invention also relates to a disposable syringe that has been produced in accordance with one of the aforesaid methods while using a prefabricated, integrated rod-and-piston unit and described above.

It will be understood that the invention is not restricted to the described and illustrated exemplifying embodiments thereof and that modifications can be made within the scope of the following Claims.

I claim:

1. A method of assembling a syringe which, when assembled, includes a rod which is intended to move reciprocatingly in relation to a syringe tube, one end of which is comprised of or can coact with a needle, a piston which can coact with the rod, and means for connecting and disconnecting the piston to and from the rod respectively, comprising the steps of:

positioning an integral rod-and-piston unit so that an extension of a center line on the rod and the piston substantially coincides with an extension of a center line on the syringe tube;

inserting the integral rod-and-piston unit into the syringe tube;

separating the rod from the piston within the syringe tube; and bringing the means for connecting and disconnecting the piston to and from the rod to a unit connecting position;

wherein the separating step includes separating said rod and piston with the aid of a separate device.

2. A method according to claim 1, wherein separation is effected by exerting pressure on the rod in the direction of said center line.

3. A method according to claim 2, wherein the separating step includes separating said rod and piston with the aid of an ultrasonic device.

4. A method according to claim 1, wherein the separating step includes separating said rod and piston with the aid of an ultrasonic device.

5. A method according to claim 1, wherein the bringing step includes first bringing the rod towards the piston and then twisting the rod relative to the piston such as to bring the unit connecting and disconnecting means into a unit connecting position.

6. A method of assembling a syringe which, when assembled, includes a rod which is arranged for reciprocating movement relative to a syringe tube, one end of which is comprised of or can coact with a needle, a piston which coacts with said rod, and means for connecting and disconnecting the piston to and from the rod, comprising the steps:

positioning an integrated rod-and-piston unit to enable said rod and piston to be separated from one another;

positioning the separated rod and piston so that a center line on the rod and on the piston substantially coincides with an extension of a center line on the syringe tube;

inserting the rod and piston into the syringe tube; and bringing the means for connecting and disconnecting the piston to and from the rod to a unit connecting position;

wherein the rod and piston are separated with the aid of a separate device.

7. A method according to claim 6 wherein the rod and piston are separated with the aid of an ultrasonic unit.

8. A method according to claim 6, wherein the bringing step includes first bringing the rod towards the piston and then twisting the rod relative to the piston such as to bring the unit connecting and disconnecting means into a unit connecting position.

9. A method according to claim 6, wherein the bringing step occurs within the syringe tube.

10. A method of assembling a syringe which, when assembled, includes a rod which is arranged for reciprocating movement relative to a syringe tube, one end of which is comprised of or can coact with a needle, a piston which coacts with said rod, and means for connecting and disconnecting the piston to and from the rod, comprising the steps:

positioning an integrated rod-and-piston unit to enable said rod and piston to be separated from one another;

positioning the separated rod and piston so that a center line on the rod and on the piston substantially coincides with an extension of a center line on the syringe tube;

inserting the rod and piston into the syringe tube; and bringing the means for connecting and disconnecting the piston to and from the rod to a unit connecting position;

wherein the rod and piston are separated by exerting pressure on the rod in the direction of said center line;

wherein the rod and piston are separated with the aid of an ultrasonic unit.

11. A method of assembling a rod and piston unit for a syringe, comprising the steps of:

forming a one-piece unit that includes a piston, a rod, and a joining element that integrally connects said piston to said rod, wherein said piston and said rod include means for connecting and disconnecting the piston and the rod;

destroying the joining element to separate the piston from the rod; and connecting the piston to the rod with the connecting and disconnecting means.

12. A method according to claim 11, wherein the forming step includes molding from plastic.

13. A unit adapted for insertion into a container included in a syringe intended for one-time use only, comprising:

a rod-unit and a piston-unit, wherein the rod-unit and the piston-unit include means for connecting and disconnecting the rod-unit to and from the piston-unit, a joining element between the rod-unit and the piston-unit, the rod-unit and the piston-unit are joined together along the joining element in the form of a single integral rod-piston unit which has been produced in a mold or like tool;

wherein the rod-unit is joined to the piston-unit by means of the joining element which is formed by mutually joined and mutually facing outer corner parts of the connecting and disconnecting means;

wherein the corner parts mutually connect with said joining element, this connection being achieved by providing in said mold a gap in which molding material will flow; and wherein the joining element is adapted to enable the joining element to be broken when separating the rod-unit and the piston-unit.

14. A unit according to claim 10, wherein an extension of a center line on the rod-unit at least substantially coincides with a center line on the piston-unit.

15. A unit according to claim 14, wherein the rod-unit is joined to the piston-unit by means of the joining element which is formed by mutually joined and mutually facing outer corner parts of the connecting and disconnecting means.

16. A unit according to claim 15, wherein the corner parts mutually connect with said joining element, this connection being achieved by providing in said mold a gap in which molding material will flow.

17. A unit according to claim 10, wherein the joining element is adapted to enable the joining element to be broken when separating the rod-unit and the piston-unit.

* * * * *